(12) United States Patent
Gustafsson et al.

(10) Patent No.: US 8,281,790 B2
(45) Date of Patent: Oct. 9, 2012

(54) SURGICAL DRAPE HAVING AN ABSORBENT EDGE

(75) Inventors: Elisabeth Gustafsson, Mölnlycke (SE); Maria Ragnarsson, Olofstorp (SE); Tove Weigel, Västra Frölunda (SE); Katarina Lager, Sävedalen (SE); Lars Alvelind, Mölnlycke (SE)

(73) Assignee: Mölnlycke Health Care AB, Göteborg (SE)

( * ) Notice: Subject to any disclaimer, the term of this patent is extended or adjusted under 35 U.S.C. 154(b) by 720 days.

(21) Appl. No.: 12/293,978

(22) PCT Filed: Mar. 20, 2007

(86) PCT No.: PCT/SE2007/050178
§ 371 (c)(1),
(2), (4) Date: Aug. 20, 2009

(87) PCT Pub. No.: WO2007/108771
PCT Pub. Date: Sep. 27, 2007

(65) Prior Publication Data
US 2010/0024831 A1 Feb. 4, 2010

(30) Foreign Application Priority Data
Mar. 22, 2006 (SE) ..................... 0600657

(51) Int. Cl.
*A61B 19/00* (2006.01)
(52) U.S. Cl. ................... 128/849; 128/850
(58) Field of Classification Search .......... 128/849, 128/846, 850–856
See application file for complete search history.

(56) References Cited

U.S. PATENT DOCUMENTS

| 3,921,627 | A | | 11/1975 | Wilson et al. | |
|---|---|---|---|---|---|
| 5,222,507 | A | * | 6/1993 | Taylor | 128/849 |
| 5,454,381 | A | | 10/1995 | DeHart | |
| 5,832,927 | A | * | 11/1998 | Wijesinghe et al. | 128/849 |
| 2005/0284487 | A1 | * | 12/2005 | Gellerstedt et al. | 128/849 |

FOREIGN PATENT DOCUMENTS
DE 4324136 10/1994
JP 2001-178742 A 7/2001

OTHER PUBLICATIONS

International search report in corresponding PCT/SE2007/050178.
Written Opinion issued on Jun. 27, 2007 for Intl. App. No. PCT/SE2007/050178, filed on Mar. 20, 2007 (Inventor—Gustafsson et al.; Applicant—Molnlycke Health Care AB; pp. 1-4).
International Preliminary Report on Patentability issued on Sep. 23, 2008 for Intl. App. No. PCT/SE2007/050178, filed on Mar. 20, 2007 (Inventor—Gustafsson et al.; Applicant—Molnlycke Health Care AB; pp. 1-5).
Office Action issued on Feb. 7, 2012 for JP Pat. App. No. 2009-501388, national phase of Intl. App. No. PCT/SE2007/050178, filed on Mar. 20, 2007 (Inventor—Gustafsson et al.; Applicant—Molnlycke Health Care AB; pp. 1-6).

* cited by examiner

*Primary Examiner* — Patricia Bianco
*Assistant Examiner* — Tarla Patel
(74) *Attorney, Agent, or Firm* — Ballard Spahr LLP

(57) ABSTRACT

A surgical drape (1) has a first absorbent region (4) on the upper side thereof. According to the invention, the first absorbent region (4) extends along at least one edge of the drape (1), the first region having a dispersion of liquid on an inclined plane better than in a region (3) or regions adjacent to the first absorbent region.

18 Claims, 2 Drawing Sheets

SURGICAL DRAPE HAVING AN ABSORBENT EDGE

TECHNICAL FIELD

The present invention relates to a surgical drape having a first absorbent region on the upper side thereof.

BACKGROUND OF THE INVENTION

Surgical drapes having an upper side with absorbent regions, such as Klinidrape® manufactured by the applicant, are known. Such a drape has often a patch of highly absorbent material in a relatively small area around the surgical site, a zone of absorbent material with a relatively high absorbent capacity surrounding said patch and reaching to an end zone with a lower absorbent capacity running along one edge or the edges of the drape. The idea behind this construction is to absorb blood and other fluids as early as possible in order to prevent spreading thereof. Drapability and strength are two important factors when designing surgical drapes and very often the construction of a drape involves a compromise between these two factors. With modern synthetic materials it is however possible to obtain highly tactile materials having a sufficient strength so that the demands on these two factors can be fulfilled without compromise. As a matter of fact it has been found that the use of highly tactile materials can make the handling of the drapes difficult, especially during the sterile draping of a patient. When packaging a drape it is folded in a certain way facilitating a sterile application of the drape on a patient. It has been found that tactile drapes have a tendency to unfold and fall apart when taken out of its package, thereby making a sterile application thereof difficult or impossible. Such drapes are also difficult to handle during the draping procedure and therefore make the draping procedure more difficult and time consuming.

With surgical drapes or towels of the type described above there is also a risk that the gown of a surgeon or another person, when leaning on the operation table and thereby on the drape, would be wetted to a strike-through by blood or other fluid absorbed in the drape.

The primary objective of the present invention is to provide a surgical drape which can absorb blood and other fluids emanating from the surgical site during a surgical intervention having an improved fluid flow. A second objective is to take advantage of the extreme good drapability of highly tactile drape materials without occurrence of the above mentioned handling problems.

SUMMARY OF THE INVENTION

This objective is obtained by a surgical drape having a first absorbent region on the upper side thereof, characterized in that said first absorbent region extends along at least one edge of the drape, said first region having a dispersion of liquid on an inclined plane better than in a region or regions adjacent to said first absorbent region. In such a drape the flow of fluid from a surgical site is improved since the fluid can spread quickly from the surgical site to the edges of said drape. Since the absorbent material is concentrated to the edge region or edge regions of the drape, the risk that the area of the drape surrounding the surgical site or surrounding an optional patch of absorbent material placed close to and enclosing the surgical site will be saturated by fluid from the surgical site is eliminated or at least essentially eliminated. The risk that a gown of a surgeon or another person, when leaning on the operation table and thereby on the drape, would be wetted to a strike-through by blood or other fluid absorbed in the drape is thereby minimized. Furthermore, the first absorbent region stiffens the edge or edges of the drape which stiffening removes the problem regarding the draping of a patient if the drape is made of a highly tactile material and thereby makes it possible to take advantage of the very good drapability of the tactile material.

According to a preferred embodiment, the dispersion of liquid on an inclined plane of said first absorbent region is less than 500 mm in length and more than 100 mm in width.

Preferably, said first absorbent region is constituted by a piece of absorbent material affixed to an edge of a basic sheet, wherein said first absorbent region along at least one edge of the drape has a width of at least 15 cm. To advantage the drape can includes a patch of absorption material applied to the upper side of the drape in a region distal from the said first absorbent region.

In an alternative embodiment, the drape includes a sheet of hydrophobic material provided with said first absorbent region on an upper side thereof.

A layer of a soft material, such as wadding, can be laminated to the lower of said sheet of hydrophobic material.

The drape has also less drapability in said first absorbent region than in other adjacent regions.

In a preferred embodiment, the drapability of the material in said first region should be more than 70% and the drapability of material in the drape in other regions of the drape should be less than 70%.

A drape according to the present invention should be dimensioned so that said first region will be situated below the edge of an operation table when the drape is draped on a patient lying on the operation table.

BRIEF DESCRIPTION OF THE DRAWINGS

The invention shall now be described with reference to the enclosed Figures, of which.

DESCRIPTION OF EMBODIMENTS

Figure 1:
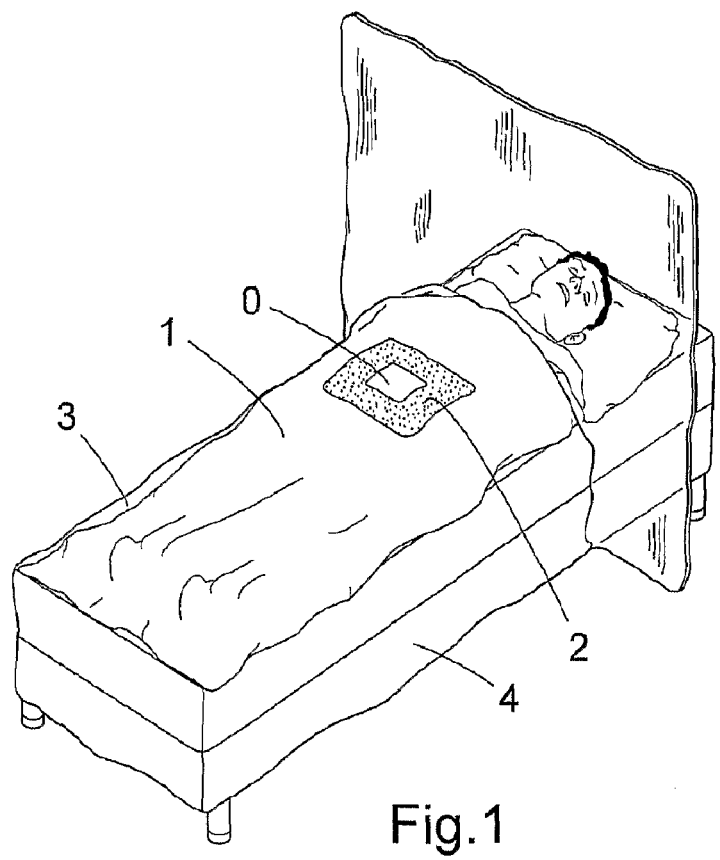
FIG. 1 schematically shows a perspective view of a patient on an operation table being draped by a surgical drape according to a first embodiment of the invention, and FIG. 2 schematically shows four surgical drapes according to a second embodiment of the invention being arranged around an intervention area.

In FIG. 1 is disclosed a drape 1 according to a first embodiment of the present invention draped on a patient lying on a operation table. Said drape has an opening O giving access to a surgical site and optionally a patch 2 of absorbent material surrounding the surgical site. The drape 1 is made of a basic sheet 3 of a highly tactile material and around the edges thereof is a piece 4 of absorbent material attached to this sheet 3.

The basic sheet 3 is preferably a nonwoven or woven material made of synthetic fibres, for example a SMS-material (spunbond-meltblown-spunbond), or a nonwoven, having one or more layers, laminated to a layer of plastic material. The fibres should be hydrophobic and can consist of polyolefins, such as polyethene (PE), polypropylene (PP) or polyester (PES) or combinations thereof. It also possible to use a plastic layer, e.g of PE, PP or a mixture therof, not being a fibre material as basic sheet. The basis weight of the sheet 3 is between 30-90 $g/m^2$, preferably between 60-80 $g/m^2$. A layer of absorbent material can be laminated to the hydrophobic material 3 or the surface thereof can be made hydrophilic but preferably this material is without absorbent layer.

The piece of absorbent material 4 attached to the sheet 3 can be a laminate of a layer of plastic material, for example PE, and an absorbent material, for example nonwoven. The layer of plastic material in this piece 4 can be separate from or integral with the basic sheet 3. The absorbent layer in this laminate 4 can consist of viscose, cotton, nonwoven material made of cellulose fibres, or other absorbent materials used for drapes or sanitary articles. The width of the piece 4 of material, i.e. the extension thereof in a direction perpendicular to the edge of the drape 1, should be 15 cm or more in order to ensure that gushes of fluid flowing from the basic sheet 3 onto the piece 4 of material can be absorbed by the absorbent material and thereby be prevented from dripping down on the floor. The piece 4 of material need not be a laminate material but can be an absorbent textile or nonwoven material even if a laminate between a plastic sheet and an absorbent material is preferred, as long as it is stiff enough.

The piece 4 of material should have a drapability of more than 70% as measured by test method EN ISO 9073-9: 1998 modified by preparation of test samples at 23±2° C. and 50±2% RH during at least 24 hours and the use of test samples which always have a diameter of 36 cm. In principal it can be said that in this method, the projected area of a test sample draped around a disc is compared with the area of the test sample in a planar condition.

The drapability of the basic sheet 3 of the drape should be less than 70%.

By providing the drape 1 with an edge material, having such low drapability or high stiffness, it has been found that the drape 1 has a relatively low tendency to unfold and fall apart when taken out of its package, thereby making a sterile application thereof on the patient fairly easy. This low drapability or high stiffness can be obtained by the absorbent layer alone or an under-laying plastic layer. The stiffness of the edge portion of the drape is of no disadvantage with regard to the draping of a patient since it is restricted to parts of the drape that do not extend over the body of the patient, the basic sheet 3 having an excellent drapability.

The concentration of absorbent material to the piece 4 of material attached to the edge of drape 3 has another advantage. When fluid escape from the surgical site O it will rapidly flow to the piece 4 of material and be absorbed by the absorbent material therein. Since the basic sheet according to the preferred embodiment is hydrophobic or has been treated to have a hydrophilic surface, the surface thereof will be almost dry immediately after a fluid flow is ended. Thereby, there is small risk that the gown of a surgeon or other person leaning over the patient and coming into contact with the basic sheet 3 of drape will be wetted by fluid, that is absorbed by drape, to such an extent that a strike-through of fluid would occur in the gown, since the absorbed fluid is present only in the edge piece 4. In order to prevent wetting of gowns or the like being in contact with the drape it is preferred that the basic sheet is constituted only by one or more layers of hydrophobic material and also that the basic sheet in use of the drape reach over the edge of an operation table. However, even if some absorbent material is present on the surface of the basic sheet, the major portion of fluid emanating from the surgical site will flow to the edge region of the drape and be absorbed by the absorbent material in this region so that the risk that the gown of a person gets wetted to a strike-trough by fluid absorbed on the surface of the basic sheet is greatly reduced. In order to reduce the possibility that fluid present on or absorbed in the basic sheet should wet the gown of a person in contact therewith, fluid emanating from the surgical site should flow as fast as possible to the edge piece 4 to be absorbed therein.

When fluid flowing downwardly from the basic sheet 3 in a stream encounters the absorbent material of the edge piece 4, it will be absorbed by the absorbent material until this material is locally saturated. The surplus of this fluid, i.e. the amount of fluid remaining after the local saturation, will continue downwardly and be locally absorbed. At the same time dry areas of the absorbent material on the sides of the locally saturated portions of the absorbent material will suck fluid from the saturated areas and distribute the absorbed fluid sideways. Gravity will also induce a downward flowing of saturated fluid into unsaturated areas of the absorbent material. This will lead to a dome-shape of the absorbed fluid in the piece 4, the top of the dome being located at the place the stream of fluid encountered the piece 4. At the base of the dome, i.e. along the lower edge of the drape 1, surface tension will prevent fluid in saturated base area of the dome from dripping down to the floor but the fluid will flow sideways along the lower edge of the drape 1 and eventually be absorbed by the absorbent material and transported away from the edge of the drape. It is to be noted that the described flowing pattern occurs when a maximum amount of fluid emanates in a gush from the surgical site. By a maximum amount of fluid is meant the maximum amount for which the drape is dimensioned to take care of. This means that most of the times fluid flowing from the surgical site will be fully absorbed by the piece 4 of material before it reaches the lower edge thereof. On the other hand, if the amount of fluid in the gush exceeds the maximum amount dimensioned for, fluid will drop on the floor. The maximum amount of fluid dimensioned for is influenced by the type of absorbent material used, the amount of absorbent material per unit area and the width of the piece 4. The properties of the absorbent material can also be influenced by treatment thereof, for example can the material be compressed in order to reduce the size of the capillaries of absorbent material.

From the foregoing it is evident that it is important that fluid emanating from the surgical site as fast as possible reach the piece 4 of absorbent material and that this piece can take care of this fluid so that it will not fall off the drape onto the floor.

In order to establish if a desired flow pattern in the basic sheet 3 and the piece 4 can be obtained, values of dispersion of liquid on an inclined plane has been measured for determining if a material is suitable as material for the basic sheet 3 and if a material is suitable for the piece 4 of absorbent edge material in accordance with a test method ID:T-218 of Mölnlycke Health Care AB, Göteborg, Sweden.

Figure 3:
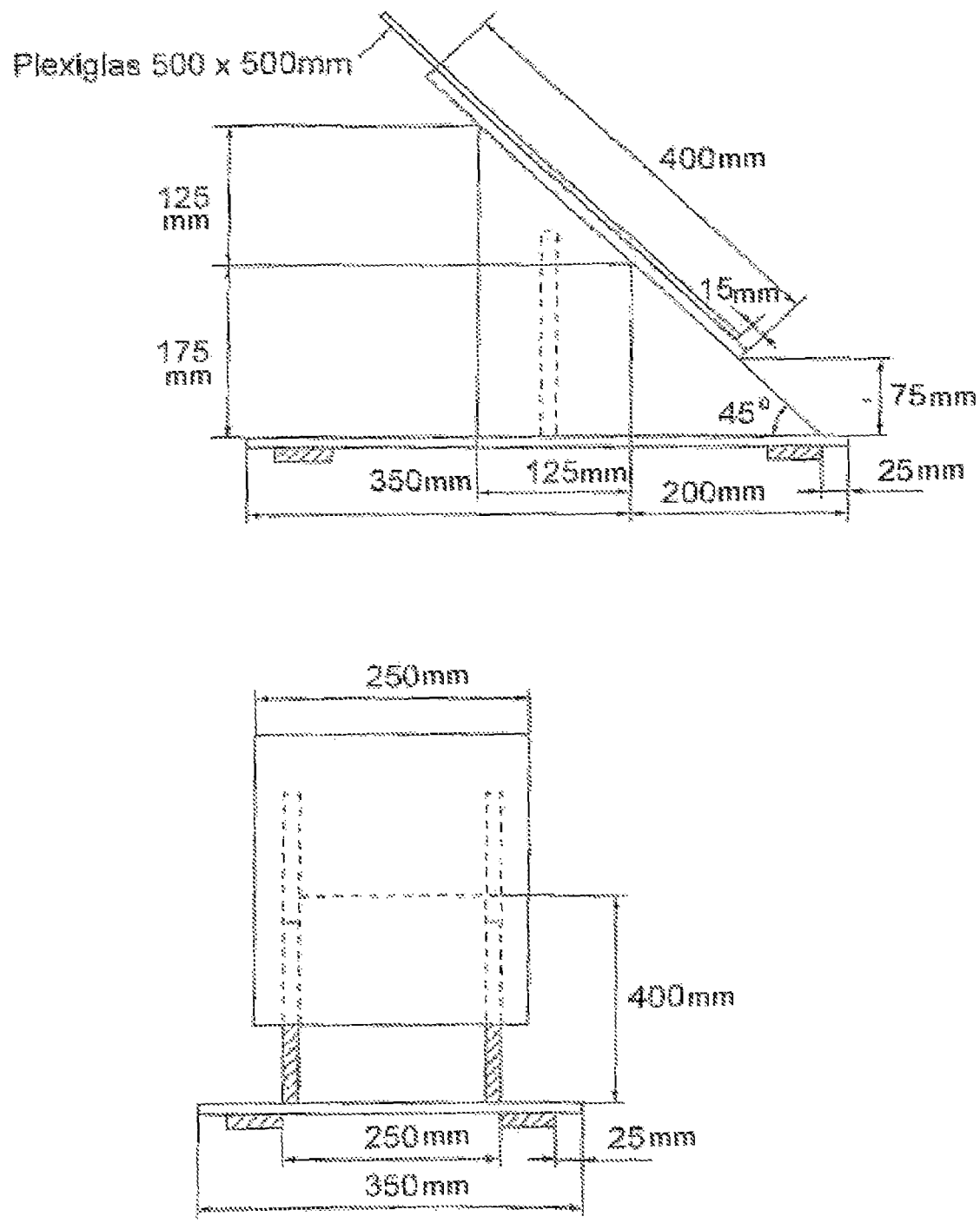
FIG. 3 schematically shows a side view and front view of a test set-up to test a sample of material on an inclined plane.

In this method a sample of 600×600 mm of the material to be tested, which has been conditioned at 23° C. and 50% RH, is fixed onto an inclined plane with an inclination of 45°, as can be seen in FIG. 3. The plane is a plexiglass plate of 500×500 mm. The sample is fixed to the Plexiglass plate with 4 clamps and then a burette provided with a slanted spout is filled with test liquid from a pump having a flow of 5 ml/17 seconds. The test liquid is a salt solution consisting of 1 g 10% Nykockin solution and 9 g NaCl per liter distilled water.

Thereafter, 5 ml of test liquid is poured onto the sample from about 5 mm above the sample and 20 mm from its upper edge.

The maximal length and the maximal width of the dispersion pattern on the sample is measured after 15 seconds and after 60 seconds.

The dispersion of liquid on an inclined plane according to said method has been made for three different materials, denoted "laminate A, B and C. "Laminate A" was a three ply laminate where the top web is constituted of a spunbond nonwoven of 30 g/m² treated with a hydrophilic agent. The total basis weight of "laminate A" was 65 g/m². "Laminate B" was a two ply laminate having a top web of spunbond nonwoven of 40 g/m² treated with the same amount of hydrophilic agent as "laminate A". The increased grammage compared to "laminate A" allows more fluid to be absorbed in "laminate B". The total basis weight of "laminate B" was 65 g/m². "Laminate C" was a two ply laminate in which the top web was a chemically bonded nonwoven of 23 g/m². This nonwoven contained 71% hydrophilic viscose fibres and 29% EVA, a hydrophilic binder substance. The total basis weight of "laminate C" was 63 g/m². The top web may be laminated to a bottom layer, exemplified but not limited to, a plastic film that is fluid impermeable. In the method the length of the dispersion of liquid was measured after 15 seconds and after 60 seconds. The drapability of the material was also measured. The results are shown in table 1.

TABLE 1

|  | Laminate A | Laminate B | Laminate C |
|---|---|---|---|
| Absorption 15 sec (mm) T-218 | >600 | 461 | 306 |
| Absorption 60 sec (mm) T-218 | >600 | 479 | 357 |
| Drapability (%) EN ISO9073-9: 1998 | 69 | 68 | 74 |

As can be seen from table 1, "laminate A" absorbed very little fluid thus allowing rapid transport to the secondary fluid storage material (piece 4) which may be a material similare to "laminate C" exhibiting very good absorption properties. "Laminate A" had also good drapability and is thus qualified as a material for a basis sheet 3 according to the invention.

"Laminate B" exhibited a good drapability as required for a sheet 3 according to the invention and also good absorption properties. However, this material is less suitable for a for a sheet 3 according to the invention since it has poor ability to rapidly transport fluid to a secondary region (piece 4 according to the invention).

"Laminate C" exhibited very good absorption properties but not so good drapability. This material is very suitable for a piece 4 according to the invention.

A material that could be used as piece 4 (or the first absorbent region) according to the present invention shall exhibit a dispersion of liquid on an inclined plane preferably being less than 500 mm.

A revised test method ID:T-218 was also made in order to investigate the amount of liquid absorbed before fluid dripped over the lower edge of the test sample. The test was performed the same way as for the dispersion measurements according to table 1 with the difference that the pump was not shut off after but delivered a continuous flow of fluid. The test was performed on two samples of each of the materials described above. The results of this revised test was that "laminate A" had absorbed 7 ml and 5.3 ml, "laminate B" 10 ml and 10 ml and "Laminate C" 25.8 and 26.3 ml. The absoption capacity of "laminate C" was thus far better than the capacity of "laminate A" and "laminate B".

The patch 2 of absorbent material surrounding the surgical site O in FIG. 1 is optional. If such a patch is used, the absorbent edge piece 4 need not be dimensioned to take care of all fluid emanating from the surgical site O. The patch 2 can be an integral part of the drape 1 or a part attached in connection with the draping of a patient. In any case, the patch should be soft and have excellent drapability and also be attached to the basic sheet in such a way that the drapability thereof will not suffer to any significant extent. For example, the patch can be a nonwoven and made of cellulose based fibres and polyolefin fibres and attached to the basic sheet by hot melt adhesive.

Figure 2:
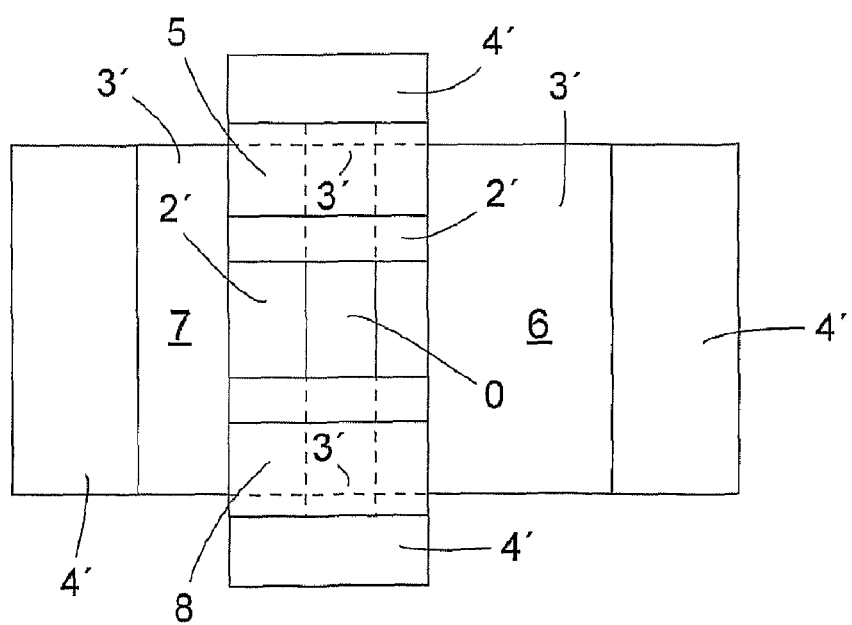

In FIG. 2, a second embodiment of the present invention is disclosed. This embodiment differs from the embodiment in FIG. 1 in that four surgical towels 5-8 are used to drape a patient instead of the surgical drape 1 according to the first embodiment. Each of these surgical towels comprises a basic sheet 3', a piece 4' of absorbent material and a patch 2' of absorbent material. These components are similar to the corresponding components in the embodiment according to FIG. 1 and are given the same reference numerals with the addition of a prime sign. In FIG. 2, the surgical towels 5-8 are arranged surrounding a surgical site O.

The embodiments shown can of course be modified in several aspects without leaving the scope of invention. For example, the invention can be applied on other types of surgical drapes intended for other types of surgical interventions than the one shown in FIG. 1, such as apertured drapes and drapes having slots. The width of the piece of absorbent material attached to the edge of the basic sheet of a surgical drape or towel can vary along the edge thereof, for example the width of this piece can be smaller in the foot end part and/or head end of the surgical drape. Moreover, the amount of absorbent material may vary in the piece of absorbent material. The drape or the basic sheet could be provided with a soft comfort sheet on the upper or/and lower side thereof. The scope of invention shall therefore only be limited by the content of the enclosed patent claims.

The invention claimed is:

1. A surgical drape comprising a first absorbent region on the upper side thereof, wherein said first absorbent region extends along at least one edge of the drape, said first absorbent region having a dispersion of liquid when measured on an inclined plane better than in a region or regions adjacent to and inward of said first absorbent region relative to the edge of the drape wherein the drape has less drapability in said first absorbent region than in other regions, wherein the drapability of material in said first absorbent region is more than 70% as measured by test method EN ISO 9073-9 1998 and the drapability of material in other regions of the drape is less than 70% as measured by said test method.

2. The surgical drape of claim 1, wherein the dispersion of liquid within said first absorbent region when positioned on a plane inclined to 45° is less than 500 mm in length after 60 seconds.

3. The surgical drape of claim 2, wherein said first absorbent region comprises a piece of absorbent material affixed to an edge of a basic sheet.

4. The surgical drape of claim 2, wherein said first absorbent region comprises a layer of absorbent material laminated to a plastic layer.

5. The surgical drape of claim 2, wherein said first absorbent region has a width of at least 15 cm measured from the edge of the drape.

6. The surgical drape of claim 2, wherein the drape further comprises a patch of absorption material applied to the upper side of the drape in a region surrounding a surgical site, said patch and being spaced distally from said first absorbent region.

7. The surgical drape of claim 2, wherein the drape comprises a sheet of hydrophobic material provided with said first absorbent region on an upper side thereof.

8. The surgical drape of claim 2, wherein a layer of a soft material is laminated to the lower side of said sheet of hydrophobic material.

9. The surgical drape of claim 2, wherein the drape has less drapability in said first absorbent region than in other regions.

10. The surgical drape of claim 2, wherein the drape is dimensioned so that said first absorbent region will be situated below the edge of an operation table when the drape is draped on a patient lying on the operation table.

11. The surgical drape of claim 1, wherein said first absorbent region comprises a piece of absorbent material affixed to an edge of a basic sheet.

12. The surgical drape of claim 3, wherein said piece of absorbent material comprises a layer of absorbent material laminated to a plastic layer.

13. The surgical drape of claim 1, wherein said first absorbent region comprises a layer of absorbent material laminated to a plastic layer.

14. The surgical drape of claim 1, wherein said first absorbent region has a width of at least 15 cm measured from the edge of the drape.

15. The surgical drape of claim 1, wherein the drape further comprises a patch of absorption material applied to the upper side of the drape in a region surrounding a surgical site, said patch being spaced distally from said first absorbent region.

16. The surgical drape of claim 1, wherein the drape comprises a sheet of hydrophobic material provided with said first absorbent region on an upper side thereof.

17. The surgical drape of claim 1, wherein a layer of a soft material is laminated to the lower side of said sheet of hydrophobic material.

18. The surgical drape of claim 1, wherein the drape is dimensioned so that said first absorbent region will be situated below the edge of an operation table when the drape is draped on a patient lying on the operation table.

* * * * *